United States Patent [19]

VanTassel et al.

[11] Patent Number: 6,126,649
[45] Date of Patent: Oct. 3, 2000

[54] STEERABLE CATHETER WITH EXTERNAL GUIDEWIRE AS CATHETER TIP DEFLECTOR

[75] Inventors: Robert A. VanTassel, Excelsior; Robert S. Schwartz; David R. Holmes, both of Rochester, all of Minn.

[73] Assignee: TransVascular, Inc., Menlo Park, Calif.

[21] Appl. No.: 09/329,386

[22] Filed: Jun. 10, 1999

[51] Int. Cl.[7] .................................................. A61M 25/01
[52] U.S. Cl. ........................................ 604/528; 604/95.04
[58] Field of Search ............................ 604/95.01, 95.04, 604/179, 523, 525, 528, 530

[56] References Cited

U.S. PATENT DOCUMENTS

| | | |
|---|---|---|
| 2,498,692 | 2/1950 | Mains . |
| 3,119,392 | 1/1964 | Zeiss . |
| 3,776,222 | 12/1973 | Smiddy . |
| 4,245,624 | 1/1981 | Komiya . |
| 4,582,181 | 4/1986 | Samson . |
| 4,826,087 | 5/1989 | Chinery . |
| 4,861,336 | 8/1989 | Helzel . |
| 4,940,062 | 7/1990 | Hampton et al. . |
| 4,976,688 | 12/1990 | Rosenblum . |
| 4,998,917 | 3/1991 | Gaiser et al. . |
| 5,098,412 | 3/1992 | Shiu . |
| 5,352,198 | 10/1994 | Goldenberg et al. . |
| 5,419,764 | 5/1995 | Roll . |
| 5,439,006 | 8/1995 | Brennen et al. . |
| 5,489,269 | 2/1996 | Aldrich et al. . |
| 5,562,619 | 10/1996 | Mirarchi et al. . |

*Primary Examiner*—A. T. Nguyen
*Attorney, Agent, or Firm*—Thomas J. Nikolai; Nikolai Mersereau and Dietz

[57] ABSTRACT

A steerable catheter in which a guidewire can serve a dual purpose of deflecting a bendable element at a distal end of the steerable catheter and as a guidewire to facilitate the placement of a working catheter within the vascular system. The guidewire is adapted to be slidingly received within routing eyelets or the like where one of such eyelets is disposed at a distal end of the bendable element and another near the proximal end thereof. The guidewire can be readily advanced in the distal direction relative to the steerable catheter, but tensioning of the guidewire at its proximal end serves to deflect and bend the bendable element.

7 Claims, 1 Drawing Sheet

STEERABLE CATHETER WITH EXTERNAL GUIDEWIRE AS CATHETER TIP DEFLECTOR

BACKGROUND OF THE INVENTION

I. Field of the Invention

This invention relates generally to catheters, and more particularly to an intravascular or other type of catheter having a deflectable distal tip portion to facilitate the steering thereof along a body lumen where the device used to deflect the tip comprises a guidewire.

II. Discussion of the Prior Art

In performing a variety of diagnostic and therapeutic procedures, it is known that an elongated, flexible catheter may be routed through the vascular system until a distal end thereof is disposed at a desired location where a measurement is to be taken or therapy delivered. Certain of these prior art catheters may have a preformed tip shape configuration to facilitate its routing. Others may have deflectable tips, such as is shown in U.S. Pat. No. 4,940,062 to Hampton, et al. Here, an internal pull-wire is contained within a lumen of the catheter and a distal end of the pull-wire is affixed to a closed end of the catheter. Tensioning of the pull-wire causes the distal tip portion to deflect at an angle to the longitudinal axis of the catheter where the extent of bending is a function of the amount of tension applied to the pull-wire. The catheter of the Hampton et al. patent has a closed distal end, precluding the use of a conventional guidewire to assist in routing and placement of the catheter. This is a distinct disadvantage in that most medical practitioners involved in interventional procedures routinely use elongated, flexible guide wires to assist in advancing a guide catheter through a patient's vascular system into the cardiac chamber, or into a coronary artery or vein.

Following the Seldinger technique, a percutaneous puncture may be made in a patient's groin using an introducer and dilator to gain access to the femoral artery. A guide catheter with a guidewire can then be advanced through the introducer and advanced through the femoral artery, the right or left iliac artery, the abdominal aorta to the ascending aorta coronary ostium in the descending aorta. From there, using fluoroscopic observation, a guidewire may be advanced through the guide catheter and into a selected coronary artery. Once the guidewire is so placed, a working catheter, such as an angioplasty balloon catheter, may be advanced over or along the guidewire into the selected coronary artery where a stenosis is to be dilated.

In addition to balloon angioplasty and angiography, another use of a steerable guide catheter is in the performance of transvascular myocardial revascularization (TMR). Here, a guide catheter must be routed through the vascular system with its distal end proximate a location of myocardial ischemia. Once the catheter is so positioned, a working catheter having a tip design to penetrate into myocardial tissue is advanced through the guide catheter and used to create one or more punctures into the myocardium to inject genes. Access to the myocardium may be via the left ventricle using a retrograde aortic approach or may utilize a coronary venous approach.

From the foregoing description, it is evident that a guide catheter with a steerable tip can advantageously be used to negotiate its way through the vascular system and into the cardiac chambers or coronary vessels. Such a guide catheter should, however, accommodate the use of a guidewire therewith. While the invention herein described finds application in various cardiac diagnostic and treatment procedures, such steerable catheters may also find use in addressing vascular occlusions in peripheral vessels or in placing electrical leads in the epidural space or in the brain.

SUMMARY OF THE INVENTION

The present invention comprises a steerable catheter having an elongated, flexible tubular body member with a proximal end, a distal end and a lumen extending therebetween. Affixed to the distal end of the tubular body member is a tubular bendable element, such as a coil spring, of a predetermined length. Guidewire routing means are affixed to the tubular body member at predetermined longitudinally spaced locations therealong for slidingly receiving a guidewire therein. A first such routing means is disposed at the distal end of the bendable element and a second routing means is disposed near a proximal end thereof. The first and second routing means are laterally offset from a longitudinal axis of the tubular body member such that tensioning of the guidewire at the proximal end thereof induces a bend in the bendable element. Because the guidewire is not fixedly attached to the bendable element, but is slidable relative to the routing means, the guidewire can be advanced independently of the steerable catheter's tubular body member until a distal end of the guidewire is at a desired treatment site. With the guidewire being held fixed in position, the steerable catheter can be advanced along the guidewire until the distal end of the bendable element reaches the distal end of the guidewire. Tensioning of the guidewire at this point then bends the bendable element with the degree of bending depending upon the amount of tension applied to the guidewire at its proximal end.

DESCRIPTION OF THE PREFERRED EMBODIMENT

Figure 1:
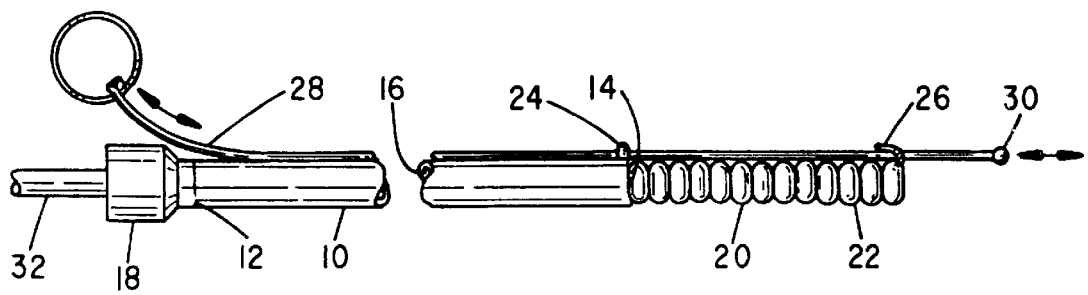
FIG. 1 is a partial side elevational view of a steerable catheter constructed in accordance with the present invention.

Turning now to FIG. 1, there is depicted an elongated, flexible, tubular catheter body member 10 having a proximal end 12, a distal end 14 and a lumen 16 extending therebetween. The catheter 10 may be made from a variety of materials including metal hypotube, polymers such as polyurethane, polyethylene, nylon or any other suitable biocompatible material. The length of the body member 10 and its cross-sectional dimensions may vary, according to the desired application.

Affixed to the proximal end 12 of the catheter body member 10 is a molded plastic hub 18 which may be of a known construction commonly used on guiding catheters for intravascular use. As such, it may include a hemostasis seal arrangement (not shown) permitting the insertion of a working catheter therethrough without attendant blood loss.

Affixed to the distal end 14 of the elongated, tubular, flexible catheter body member 10 is a tubular bendable element 20, here shown as a helical coil 22 of a predetermined length and whose outer diameter is approximately that of the body member 10. The helical coil 22 may comprise a suitable metal such as NITINOL®, MP21 alloy. ELGILOY®, spring steel or it may also be formed from a medical-grade plastic. Irrespective of the material used, the bendable element 20 is such that it can be bent 90° or more from the longitudinal axis of the catheter body member without kinking and occluding the central lumen defined by the helical coil 22. A soft, annular elastomeric tip 23 is appropriately bonded to the distal end of the bendable element to render the catheter tip more atraumatic.

Affixed to the distal end 14 of the tubular body member is a first routing means 24 which, in FIG. 1, comprises a tab of soft, flexible elastomeric material suitably bonded to the exterior wall of the catheter body member 10. A small hole of a diameter slightly larger than the diameter of a guidewire extends through the tab. A second routing means 26 in the form of a similar tab is affixed to the distal end of the bendable element 20. By utilizing a soft elastomer such as silicone rubber for the tabs, they will not injure the endothelial lining of the blood vessels as the catheter is being advanced therealong.

With continued reference to FIG. 1, an elongated flexible guidewire 28 is used in conjunction with the catheter to function as a steering element. The guidewire 28 is of known construction and, in the embodiment of FIG. 1, it extends along the length of the catheter, passing through the first and second routing means 24 and 26 and terminating in a bulbous, soft atraumatic tip 30 at its distal end. The bulbous tip is greater in size than the central openings in the flexible tabs 24 and 26. The guidewire, however, is free to slide in a distal direction through the routing means 24 and 26, allowing the guidewire 28 to function in a normal manner when advancing an intravascular catheter through a patient's tortuous coronary anatomy.

Figure 2:
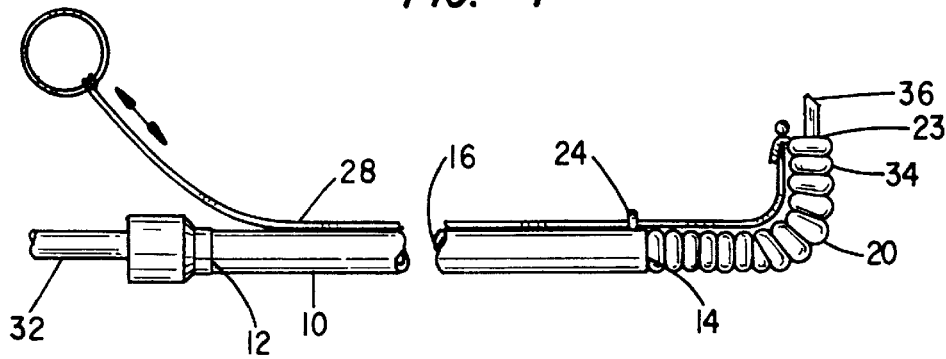
FIG. 2 is a side elevational view of the catheter of FIG. 1 when a tension force is applied at the proximal end of the guidewire.

Referring next to FIG. 2, it can be seen that by tensioning the guidewire 28, the soft, bulbous tip 30 on the guidewire is brought into engagement with the second routing means 26 and because of the size of the bulbus tip, it is unable to pass through the aperture formed in the tab. Continued tensioning of the guidewire 28 pulls on the tab and imparts a deflection of the bendable element 20 where the degree of bending or deflection depends upon the amount of tension applied. While only a single guidewire is required for both placement of the catheter tip and bending thereof, it is, of course, possible to use two guidewires, one for catheter placement and the other for bending the tip.

A working catheter 32 is adapted to be passed through the central lumen of the catheter body member 10 and the helical coil 22 to exit the distal end 34 of the bendable element 20 and the atraumatic tip member 23. Thus, for example, if the procedure in question is a direct myocardial revascularization, the guide catheter 10 may be advanced through the vascular system until the distal end of the device is disposed within a selected coronary vessel or in a ventricular chamber, at which time the guidewire 28 may be tensioned until the distal end thereof is directly pointing at myocardial tissue. Next, a working catheter 32 having a tissue penetrating tip 36 or a drug/gene delivery port may be forced out the distal end 34 of the bendable element 20 to form a hole in the myocardial tissue or to locally apply a drug/gene material thereto. Since the working catheter 32 forms no part of the present invention, it is not deemed necessary to describe the distal structure for penetrating tissue in detail. Suffice it to say, it may comprise an electrode for performing monopolar or bipolar electrosurgery. In this regard, reference is made to applicants' copending application Ser. No. 09/009,135 filed Jan. 20, 1998 and entitled "Device for Forming Holes in Tissue" for a description of such a working catheter.

Figure 3:
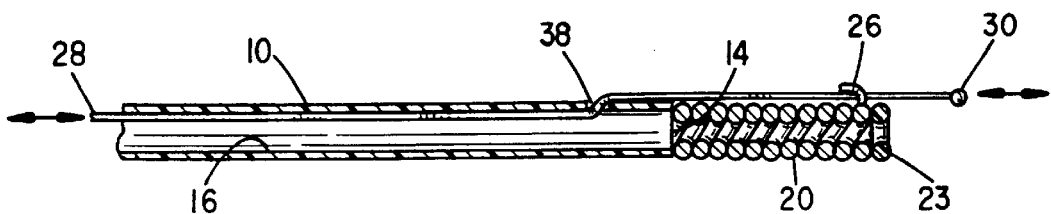
FIG. 3 illustrates the distal end portion of a guiding catheter made in accordance with an alternative embodiment of the invention.

In the embodiments shown in FIGS. 1 and 2, the guidewire 28 is routed external to the catheter body member 10 along its entire length. In the embodiment of FIG. 3, the guidewire 28 is routed through the lumen 16 of the tubular body member 10 and a bore 38 is formed through the side wall of the catheter 10 proximate the distal end 14 thereof. The guidewire 28 passes through this routing means (bore 38) and, thence, along the bendable element 20 and through the second routing means (flexible tab 26) as in the earlier embodiment. Again, the guidewire 28 can be used in a conventional way in assisting in placement of the catheter 10, but when tension is applied to the guidewire at its proximal end, the bendable element 20 will be made to deflect in the manner already explained.

In the embodiment of FIG. 3, the guidewire 28 is shown as passing through the working lumen 16 of the catheter 10 as a routing means. Those skilled in the art can appreciate that the catheter body member 10 can be extruded so as to include a working lumen and a separate guidewire lumen and in this arrangement the bore 38 need only extend through the wall of the catheter into the guidewire lumen.

A simple clamping mechanism may be affixed to the hub 18 to keep the tip bent at any desired angle while using the guiding catheter of this invention. The guidewire may be tensional, then rapidly clamped in place in its taut condition.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, more than one set of eyelets can be affixed to the guide catheter at circumferentially spaced location to accommodate additional guide/pull wires to allow greater directionality control of the bendable element.

What is claimed is:

1. A steerable catheter, comprising:
   (a) an elongated, flexible, tubular body member having a proximal end, a distal end and a lumen extending therebetween;
   (b) a tubular bendable element of a predetermined length coaxially disposed on the tubular body member;
   (c) a guidewire having a proximal end and a bulbus distal end; and
   (d) routing means on the tubular body member at predetermined longitudinally spaced locations therealong for slidingly receiving the guidewire therein, with one said routing means at a distal end of the bendable element and another routing means disposed near a proximal end of the bendable element, the routing means being laterally offset from a longitudinal axis of the tubular body member such that tensioning of the guidewire at the proximal end thereof induces a bend in the bendable element.

2. The steerable catheter as in claim 1 wherein said routing means comprise apertured tabs disposed external to the lumen of the tubular body member.

3. The steerable catheter as in claim 1 wherein one of said routing means comprises a bore formed through a wall of the tubular body member into the lumen thereof near said proximal end of the bendable element.

4. The steerable catheter as in claim 3 wherein the guidewire extends through the lumen of the tubular body member from the proximal end thereof and out through said bore.

5. The steerable catheter as in claim 2 wherein the bulbus distal end of the guidewire is of a radial dimension greater than a diameter of the apertures of said tabs.

6. The steerable catheter as in claim 5 wherein the bulbous distal end of the guidewire is a soft, atraumatic tip member.

7. The steerable catheter as in claim 2 wherein the apertured tabs comprise a soft elastomeric material.

* * * * *